United States Patent
Koo et al.

(10) Patent No.: US 9,304,104 B2
(45) Date of Patent: Apr. 5, 2016

(54) ION SENSITIVE FIELD EFFECT TRANSISTOR

(71) Applicant: X-FAB Semiconductor Foundries AG, Erfurt (DE)

(72) Inventors: Sang Sool Koo, Sarawak (MY); Ling Gang Fang, Sarawak (MY)

(73) Assignee: X-FAB SEMICONDUCTOR FOUNDRIES AG, Erfurt (DE)

( * ) Notice: Subject to any disclaimer, the term of this patent is extended or adjusted under 35 U.S.C. 154(b) by 0 days.

(21) Appl. No.: 14/072,908

(22) Filed: Nov. 6, 2013

(65) Prior Publication Data

US 2014/0061729 A1    Mar. 6, 2014

Related U.S. Application Data

(63) Continuation of application No. PCT/EP2011/057359, filed on May 6, 2011.

(51) Int. Cl.
*G01N 27/414* (2006.01)

(52) U.S. Cl.
CPC .................. *G01N 27/4148* (2013.01)

(58) Field of Classification Search
CPC .................................... G01N 27/4248
USPC .......................................... 257/253
See application file for complete search history.

(56) References Cited

U.S. PATENT DOCUMENTS

| | | | |
|---|---|---|---|
| 8,858,782 B2 * | 10/2014 | Fife | 205/793.5 |
| 2006/0035400 A1 * | 2/2006 | Wu et al. | 438/49 |
| 2010/0052080 A1 * | 3/2010 | Garcia Tello et al. | 257/414 |
| 2010/0300895 A1 * | 12/2010 | Nobile et al. | 205/775 |
| 2013/0089466 A1 * | 4/2013 | Hinz et al. | 422/69 |

FOREIGN PATENT DOCUMENTS

| | | |
|---|---|---|
| EP | 1729121 A1 | 12/2006 |
| WO | 2009151309 A1 | 12/2009 |
| WO | 2011040803 A1 | 4/2011 |

OTHER PUBLICATIONS

International Search Report for corresponding application PCT/EP2011/057359 filed May 6, 2011; Mail date Jan. 25, 2012.
Themistoklis Prodromakis, "Exploiting CMOS Technology to Enhance the Performance of ISFET Sensors", IEEE Electron Device Letters, vol. 31, No. 9. Sep. 2010, pp. 1053-1055.
Written Opinion for corresponding application PCT/EP2011/057359 filed May 6, 2011; Mail date Jan. 25, 2012.

* cited by examiner

*Primary Examiner* — William Coleman
(74) *Attorney, Agent, or Firm* — Nixon & Vanderhye PC

(57) ABSTRACT

A CMOS or bipolar based Ion Sensitive Field Effect Transistor (ISFET) comprising an ion sensitive recess for holding a liquid wherein the recess is formed at least partly on top of a gate of the transistor. There is also provided a method of manufacturing an I on Sensitive Field Effect Transistor (ISFET) utilizing CMOS processing steps, the method comprising forming an ion sensitive recess for holding a liquid at least partly on top of a gate of the transistor.

25 Claims, 10 Drawing Sheets

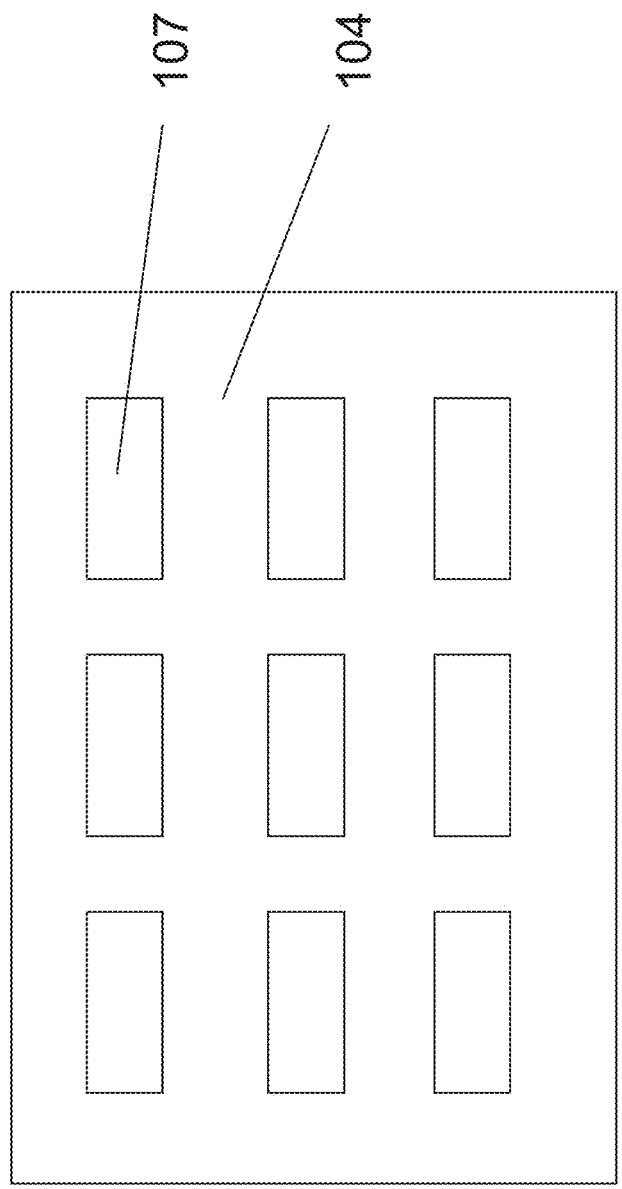

ION SENSITIVE FIELD EFFECT TRANSISTOR

CROSS REFERENCE TO RELATED APPLICATIONS

This application is a continuation of International Patent Application Number PCT/EP2011/057359 filed on 6 May 2011, the contents of which are herein incorporated by reference in their entirety.

TECHNICAL FIELD

The present invention relates to an Ion Sensitive Field Effect Transistor (ISFET), and in particular to an ISFET manufactured utilizing CMOS or bipolar processing steps.

BACKGROUND

Electronic devices and components have found numerous applications in measurement and monitoring of chemical or biological reactions such as detecting concentration, presence and activity of particular ions, enzymes, antibodies, antigens, hormones and gases. One such electronic device is referred to as an Ion Sensitive Field Effect Transistor, often denoted in the relevant literature as ISFET. This device facilitates the measurement, for example, of a hydrogen ion concentration (i.e. pH) in a solution.

FIG. 1 is a schematic cross-section of a conventional ISFET. This device is similar to a MOSFET and comprises a semiconductor substrate 141, a source 147 and a drain 145. The source 147 is spaced from the drain 145 and both are located near the surface of substrate 141. A channel region 152 is located between the source 147 and the drain 145 in the substrate 141. Inter alia in the channel region 152, the surface of the substrate 141 is covered by an insulator 101 and an ion sensitive thin layer or membrane 150 on top of the insulator 101. When the ion sensitive membrane 150 is exposed to an ionic solution, the surface potential is changed to vary the conductance of the channel region 152. By measuring the current between the source 147 and the drain 145, information such as the ion concentration of a chemical or biological reaction can be derived.

Another structure has been demonstrated which uses a MOSFET structure and connects a gate poly and an ion sensitive membrane by metal. When the surface potential of the membrane is changed due to the ion concentration or pH value of the solution, the gate voltage of the MOSFET is also changed. Information about chemical and biological reactions can then be extracted by monitoring the electric signal from the MOSFET.

A conventional ISFET needs a micro-well or recess for the chemical solutions. In this conventional ISFET, the recess needs to be well connected to the channel area of the ISFET. Further, a discrete signal readout circuit is generally employed for analyzing the signal readout from the conventional ISFET. The discrete signal readout circuit is arranged separately (i.e. not on the same chip) and connected to the conventional ISFET. Normally a printed circuit board (PCB) or wiring is used for connecting the discrete read out circuit with the conventional ISFET. The inventors have appreciated that no techniques exist which combine a conventional ISFET with signal on chip (SOC) technology using a standard CMOS process.

BRIEF SUMMARY

The present inventors have found that the above conventional technique may result in relatively high manufacturing costs and increased noise in the readout.

It is an aim of certain embodiments of the present invention to provide an ISFET structure which improves signal readout performance and reduces manufacturing cost.

According to one aspect of the present invention there is provided a CMOS or bipolar based Ion Sensitive Field Effect Transistor (ISFET) comprising an ion sensitive recess for holding a liquid wherein the recess is formed at least partly on top of a gate of the transistor.

According to another aspect of the present invention there is provided a method of manufacturing an Ion Sensitive Field Effect Transistor (ISFET) utilizing CMOS or bipolar processing steps, the method comprising forming an ion sensitive recess for holding a liquid at least partly on top of a gate of the transistor.

Preferably, the recess is formed directly on a surface of the gate. In some embodiments, a minimum contact area between the gate surface and the recess in a 0.35 µm CMOS technology is about 10 or 16 µm². Alternatively, one or more additional layers may be arranged between the gate and the recess surface. The additional layer(s) may comprise a material which is selected from any of: titanium nitride (TiN), silicon oxide nitride (SiON), silicon oxide ($SiO_2$) or a metal. Such an additional layer may improve the performance of the ISFET. Alternatively, the recess may be arranged such that there are interlayer dielectric and intermetal dielectric between the recess and gate.

The gate may consist of an insulator. Alternatively, the gate consists of an insulator and a poly gate on top of the insulator.

In some embodiments, the present invention provides a new method for integrating the ISFET in a standard CMOS or bipolar process. These embodiments comprise: (1) building up a standard CMOS or bipolar device with inter-connect metal and inter-metal dielectric films on a semiconductor substrate; (2) patterning and etching away the dielectric above an area of the ISFET down to an insulator or a poly gate; and (3) depositing an ion sensitive membrane such as a silicon nitride film covering the insulator gate oxide or poly gate. A standard bipolar device can be used in the signal read out circuit of the ISFET.

Advantageously, the integrated CMOS or bipolar process can be optimized such that the ISFET provides high performance ion detection. The CMOS or bipolar based ISFET according to embodiments of the invention enables the ion sensitive recess and signal readout circuit to be integrated within a single chip. Since the signal transmission and processing are performed on the same chip, these operations are relatively fast and produce less noise than the conventional ISFET. As a result, the signal readout or sensitivity of the ISFET is improved. The improvement in the signal readout or sensitivity of the ISFET is particularly noticeable if the ion sensitive recess is fabricated directly on top of the gate of the ISFET. The utilization of the standard CMOS process may also result in low manufacturing cost. Furthermore, the invention enables the ISFET fabrication in arrays. Therefore, the on-die analysis of a biological reaction and ion concentration becomes easier and cheaper.

BRIEF DESCRIPTION OF THE DRAWINGS

Some embodiments of the invention will now be described by way of example only and with reference to the accompanying drawings, in which:

FIG. 8b shows an alternative top view; and

DETAILED DESCRIPTION

Figure 2:
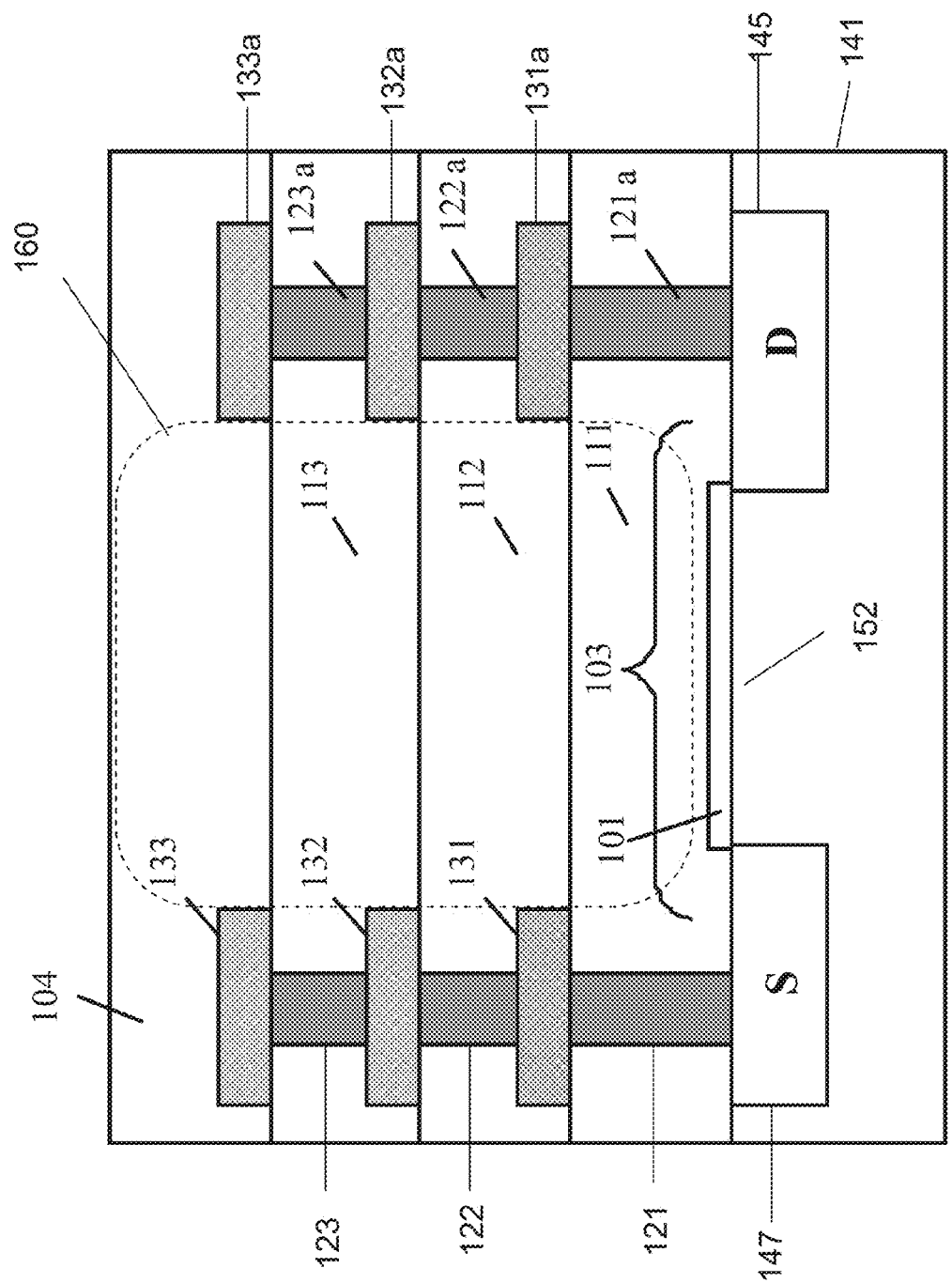
FIG. 2 is a schematic cross section of an ISFET at one stage of the fabrication according to a first embodiment of the present invention.

FIG. 2 is a schematic cross section of an ISFET at one stage of the fabrication according to a first embodiment of the present invention. A basic CMOS device is provided comprising a semiconductor substrate 141 having a source 147, a drain 145 and a channel region 152 between the source 147 and the drain 145. A gate consisting of an insulator 101 is located on top of the channel region 152. In certain embodiments, the thickness of the insulator is not less than about 5 nm and is not more than about 150 nm. The thickness of the insulator is preferably about 50 nm or 55 nm. The device also comprises inter-layer dielectric (ILD) 111 covering the insulator 101 and the substrate 141. Inter-metal dielectrics (IMD) 112, 113 are provided on top of the ILD 111. Inter metals 131 and 131a are provided on top of the ILD 111 within IMD 112. Inter metal 131 is connected with the source 147 by contact plug 121, and inter metal 131a is connected with the drain 145 by contact plug 121a. Further inter metals 132, 132a and 133, 133a are located on top of IMDs 112 and 113. Inter metals 131 and 132 are connected with one another by inter layer via 122, and inter metals 131a and 132a are connected with one another by inter layer via 122a. Similarly, inter metal 132 and top inter metal 133 are connected by inter layer via 123, and inter metal 132a and top inter metal 133a are connected by inter layer via 123a. A passivation layer 104 is provided on top of IMD 113.

In the CMOS device of FIG. 2, the source 147, drain 145, channel region 152 and insulator layer 101 are also parasitically fabricated at the same time with the CMOS process. It will be appreciated that, in the CMOS process, the insulator layer (gate oxide), poly gate, channel implant, source and drain can be fabricated using a standard process for a MOS device. This standard process can also be utilized to fabricate the ISFET. The device is connected with inter metals 131, 131a, 132, 132a, 133, 133a and contact plugs 121, 121a, inter layer vias 122, 122a, 123, 123a for the electric monitoring. A volume 160 is defined over insulator 101 of the gate, over an area 103. No metal connections are located in this volume 160. This area 103 is therefore only covered by ILD 111, IMDs 112 and 113 and passivation layer 104 during the standard CMOS manufacturing process.

Figure 1:
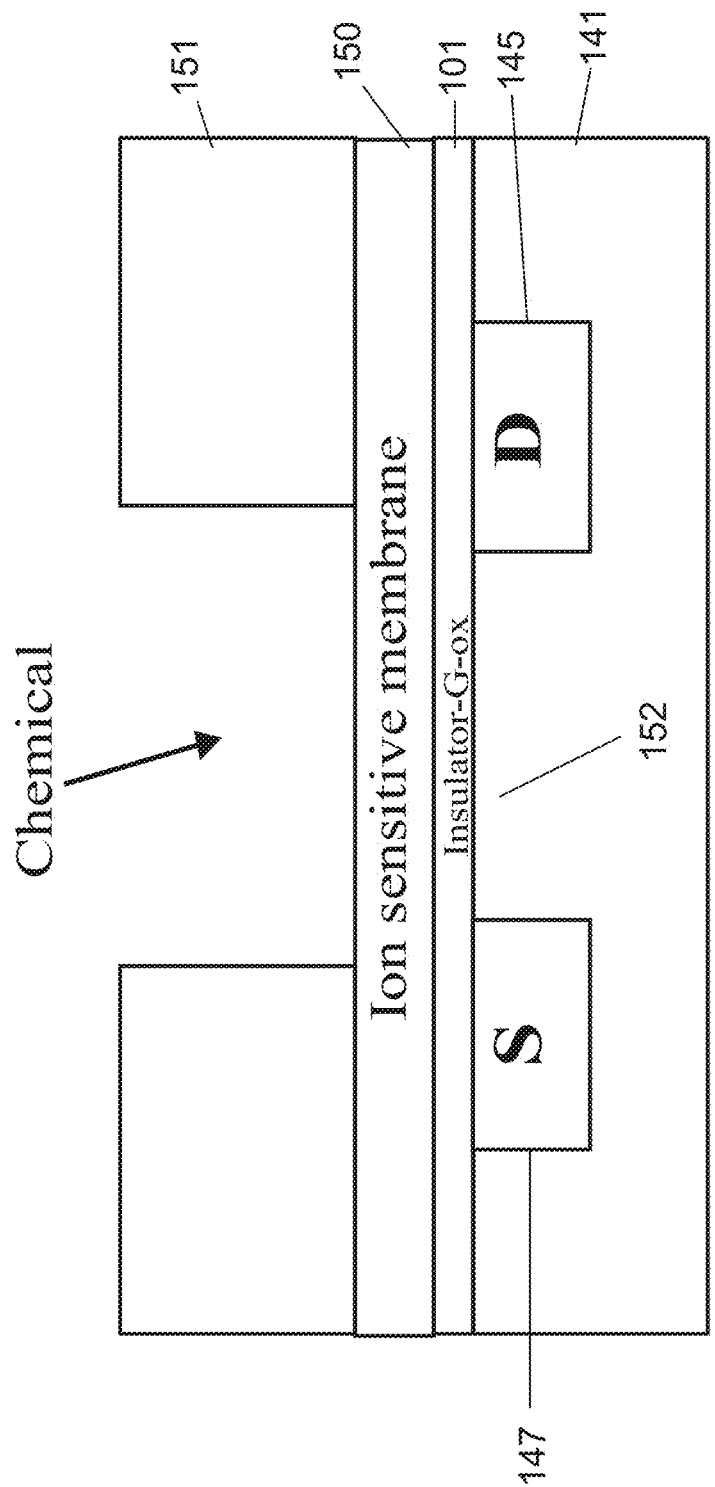
FIG. 1 is a schematic cross-section of a conventional ISFET.
Figure 3:
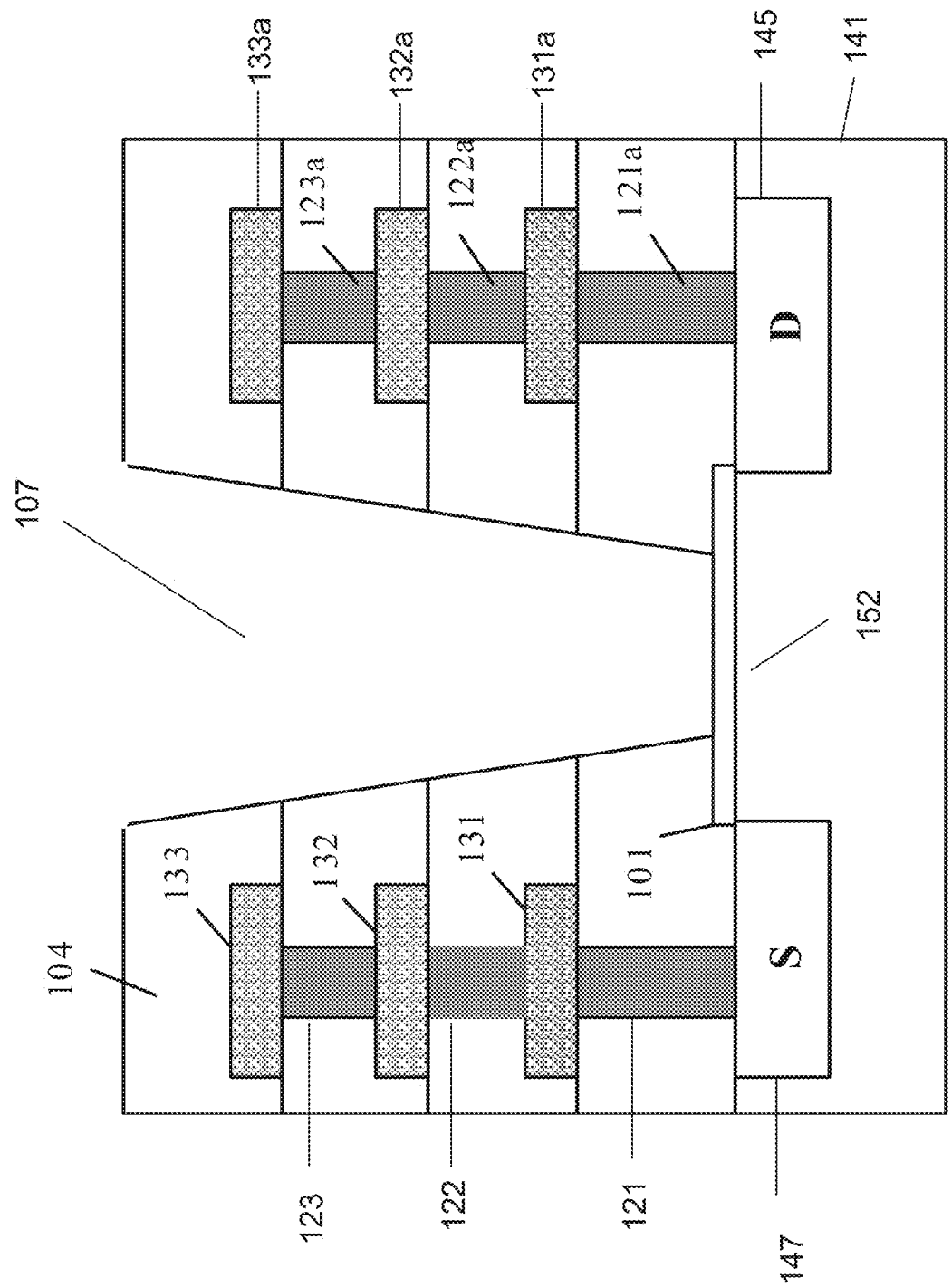
FIG. 3 is a schematic cross section of an ISFET at a second stage of the fabrication according to the first embodiment of the present invention.

FIG. 3 is a schematic cross section of an ISFET at a second stage of the fabrication according to the first embodiment of the present invention. At this stage, the process includes opening a window or recess 107 by patterning the area 103 (as shown in FIG. 1) over the gate and then by etching the dielectric layers (ILD 111, IMDs 112, 113 of FIG. 1) of the area 103. The etching process may be performed by a dry etch technique, a wet etch technique or an optical window etch technique. The etching process stops on the insulator 101 of the gate.

It will be appreciated that according to a variant the second stage of the fabrication may include the sequential steps of: etching the entire passivation layer 104 along with inter-layer metals 133, and 133a; etching the entire IMD 133 with inter metals 132 and 132a; etching the area 103 down to the insulator 101 to open a recess 107 by the OPTO window etch technique.

Figure 4:
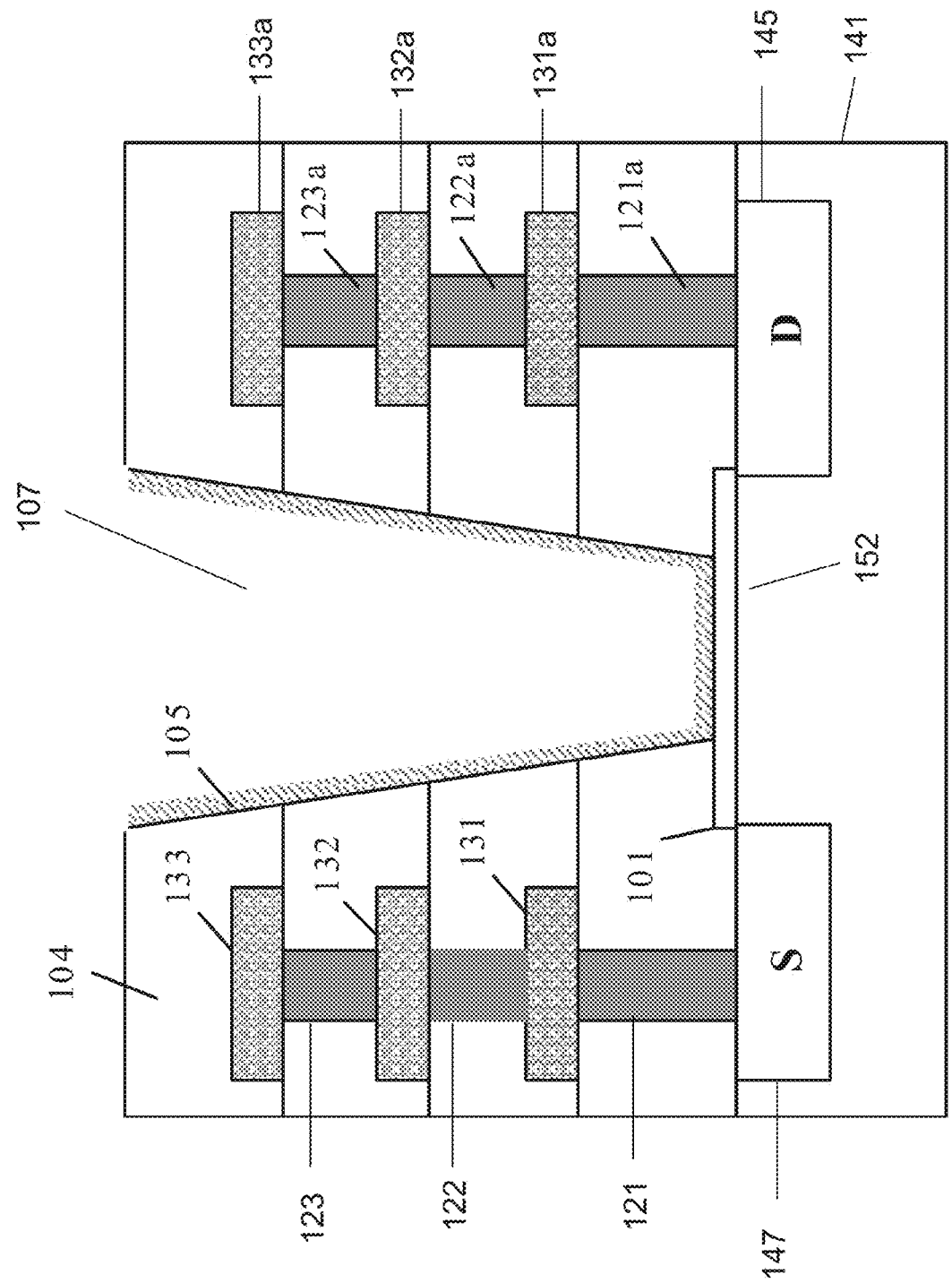
FIG. 4 is a schematic cross section of an ISFET at a third stage of the fabrication according to the first embodiment of the present invention.

FIG. 4 is a schematic cross section of an ISFET at a third stage of the fabrication according to the first embodiment of the present invention. At this stage, an ion sensitive membrane or thin film 105 is deposited on at least a portion of the surface of the recess 107. Preferably, the membrane 105 is deposited over the entire surface of the recess 107 and connects to at least a part of the surface of the insulator 101. It will be appreciated that according to a variant the membrane 105 may only cover the insulator 101 rather than fully covering the whole recess 107. The membrane 105 may comprise any one or more of a variety of different materials to facilitate sensitivity to particular ions. For example, silicon nitride or silicon oxynitride generally provides sensitivity to hydrogen ion concentration (pH).

At a final stage, the CMOS device (or the entire CMOS wafer) can be further processed by removing the passivation at a pad area, which is subsequently used for wire bonding. It will be appreciated that this process can also be performed before the ISFET recess opening and membrane deposition.

Figure 5:
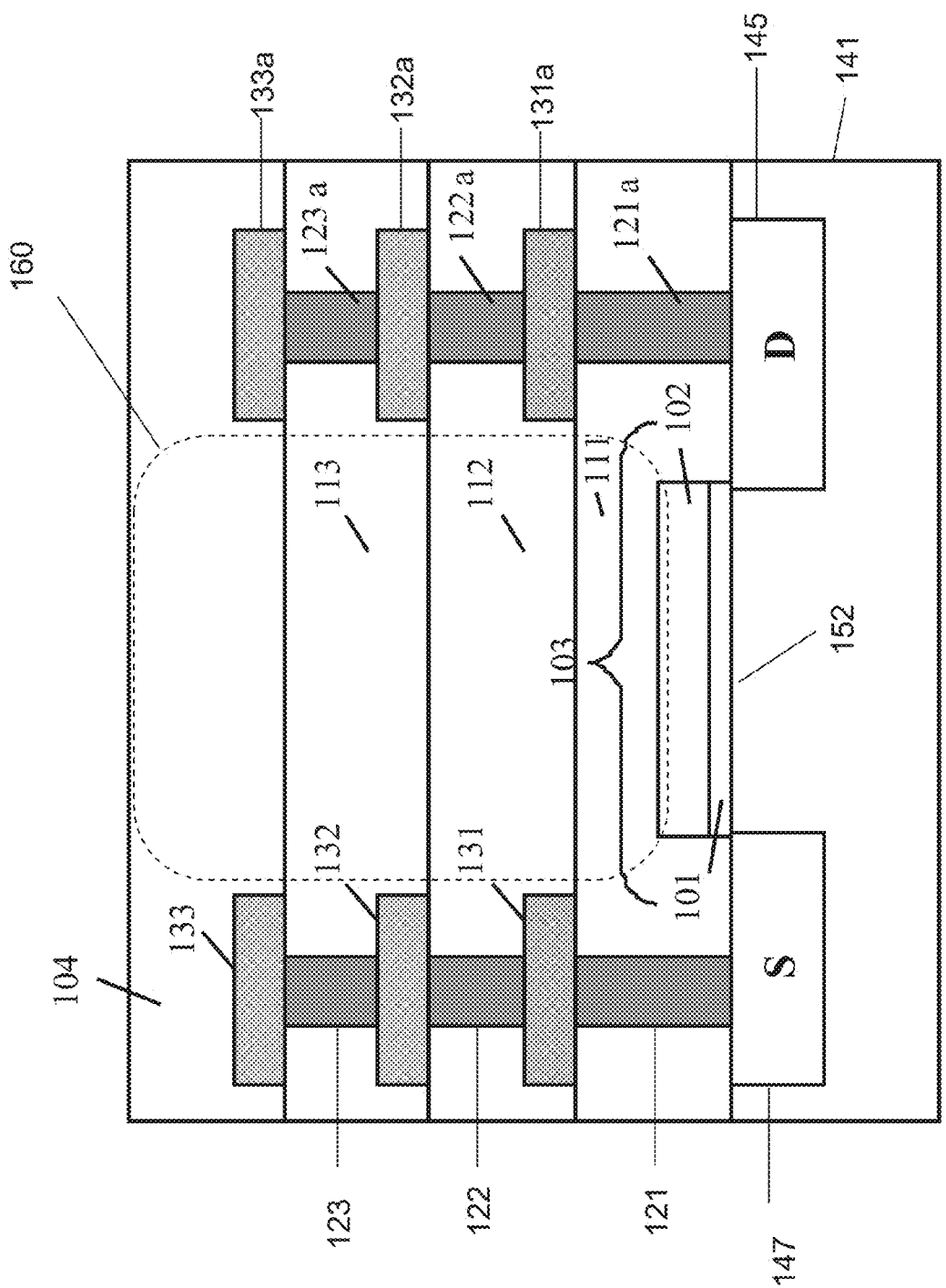
FIG. 5 is a schematic cross section of an ISFET at one stage of the fabrication according to a second embodiment of the present invention.

FIG. 5 is a schematic cross section of an ISFET at one stage of the fabrication according to a second embodiment of the present invention. All the features of the CMOS device of FIG. 5 are similar to those of the CMOS device of FIG. 2, except that an additional poly gate 102 is provided on top of the insulator 101.

Figure 6:
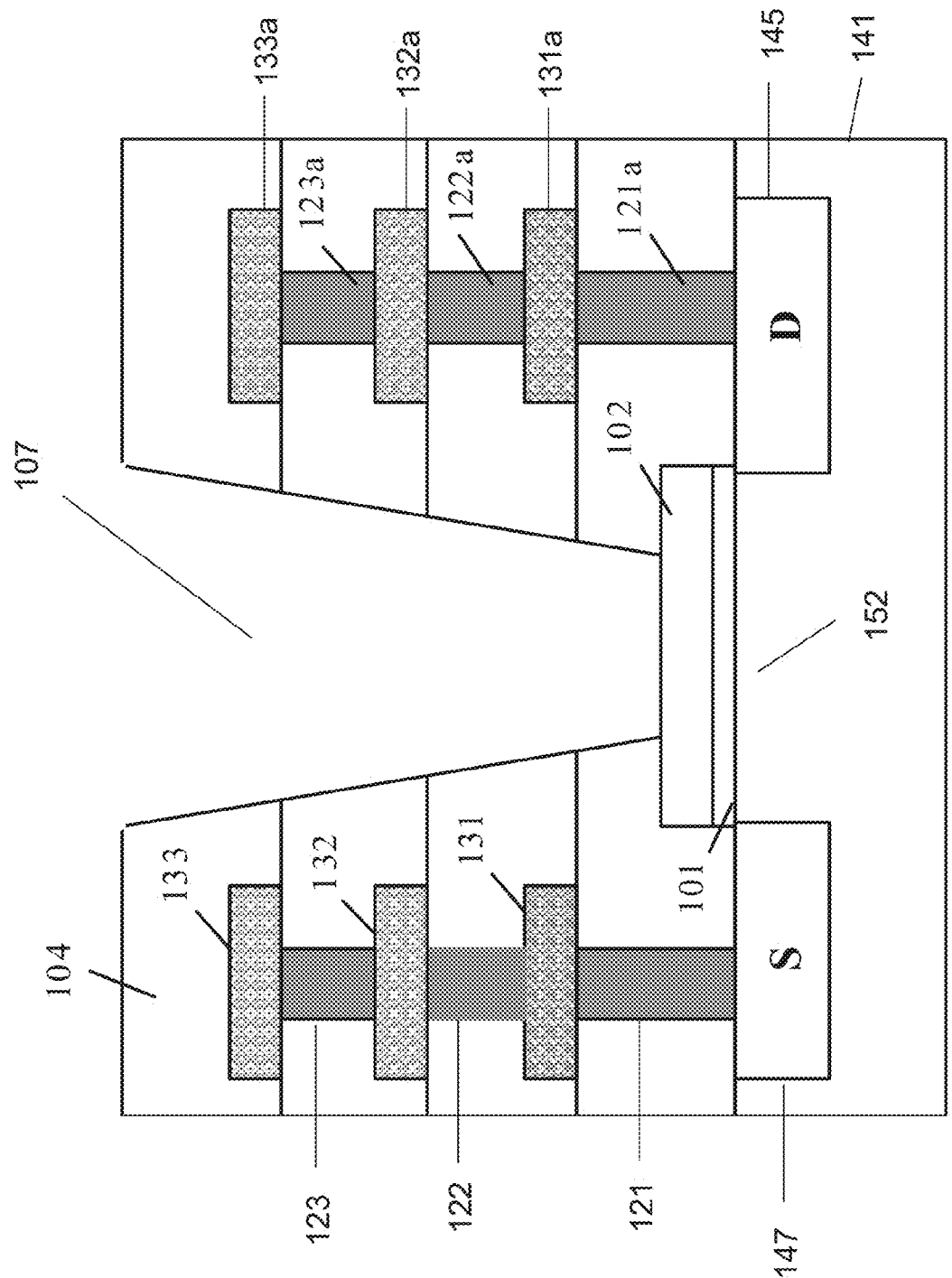
FIG. 6 is a schematic cross section of an ISFET at a second stage of the fabrication according to the second embodiment of the present invention.

FIG. 6 is a schematic cross section of an ISFET at a second stage of the fabrication according to the second embodiment of the present invention. The fabrication steps for this embodiment are the same as those described in relation to FIG. 3, except that the etching of the dielectric area 103 (of FIG. 5) is carried out down to the surface of the poly gate 102.

Figure 7:
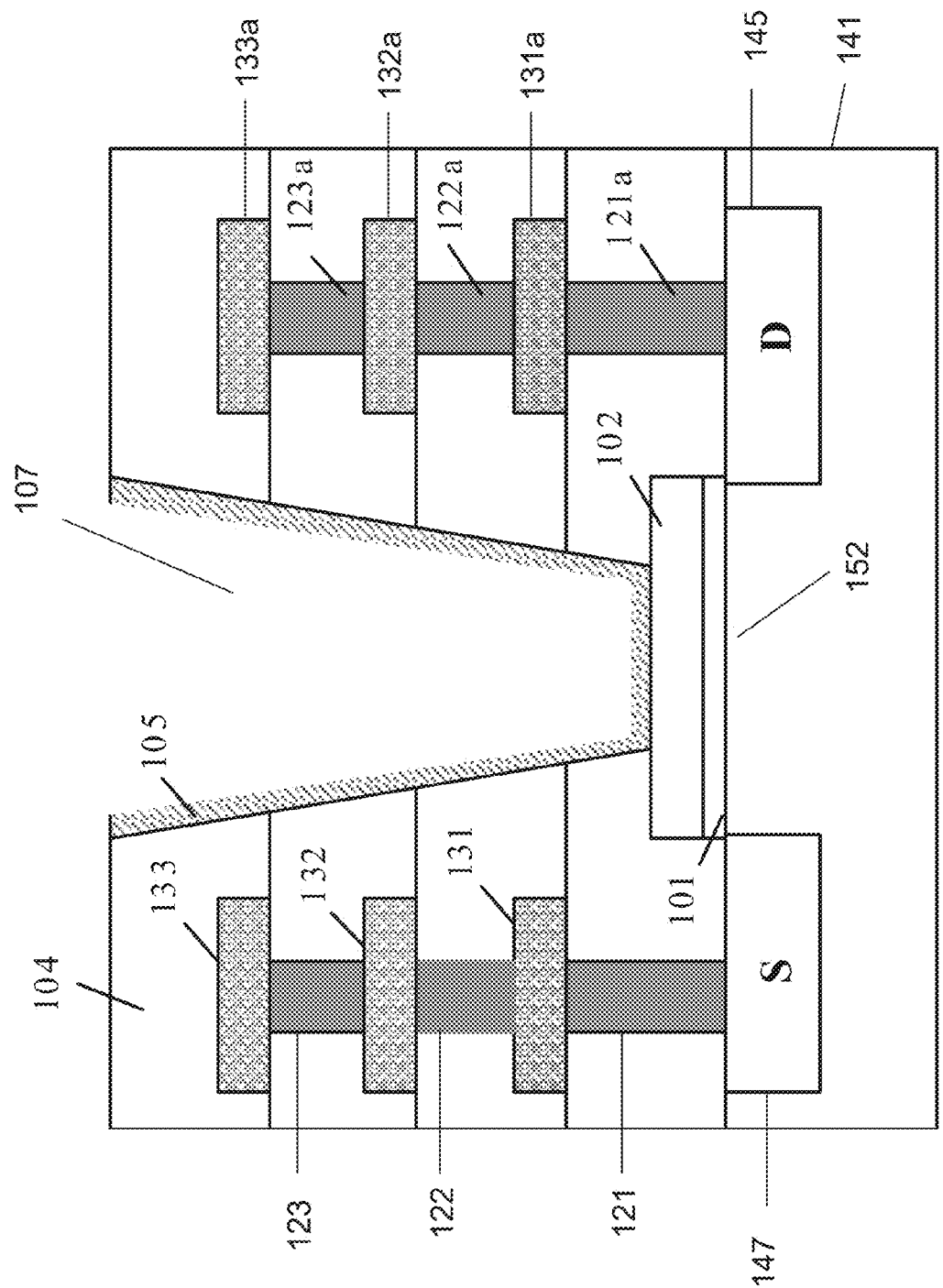
FIG. 7 is a schematic cross section of an ISFET at a third stage of the fabrication according to the second embodiment of the present invention.

FIG. 7 is a schematic cross section of an ISFET at a third stage of the fabrication according to the second embodiment of the present invention. The fabrication steps for this embodiment are also the same as those described in relation to FIG. 4, except that the ion sensitive membrane 105 is deposited over the entire recess surface to connect it with the surface of the poly gate 102.

Figure 8A:
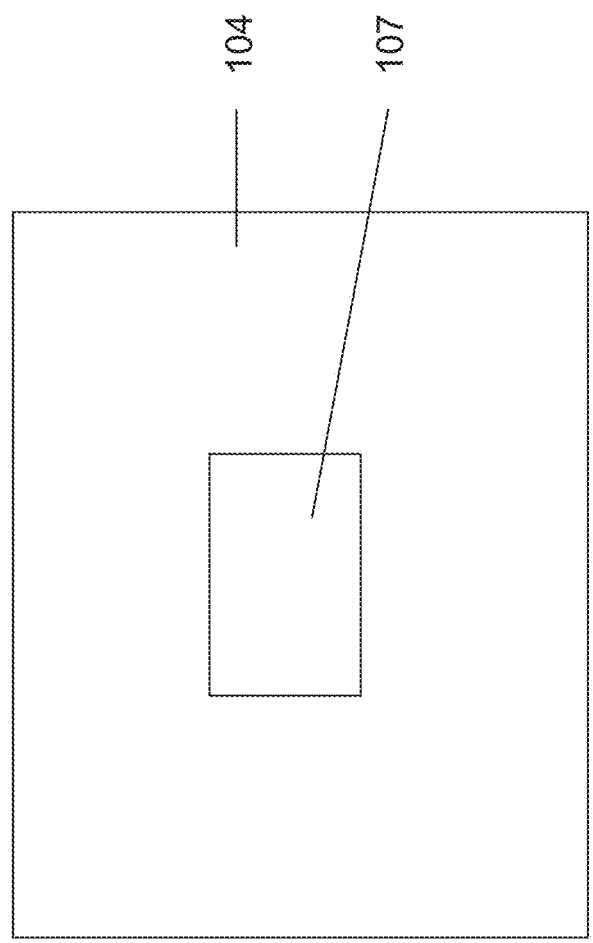
FIG. 8a shows a top view of an ISFET according to the present invention.

FIG. 8a shows a top view of an ISFET such as the ISFET of FIG. 7. Only the passivation layer 104 and the recess 107 are shown. In this embodiment, the recess 107 is fully surrounded by the passivation layer 104, i.e. the recess 107 is surrounded by five sides of the ISFET (four laterally, and the bottom of the recess).

FIG. 8b shows a top view of an ISFET arrangement having an array of ISFETs. In this arrangement, each ISFET of the array is the same as the ISFET of FIG. 7. Only the passivation layer 104 and the recess 107 are shown. In this embodiment, the recess 107 is fully surrounded by the passivation layer 104, i.e. the recess 107 is surrounded by five sides of the ISFET (four laterally, and the bottom of the recess).

Figure 8C:
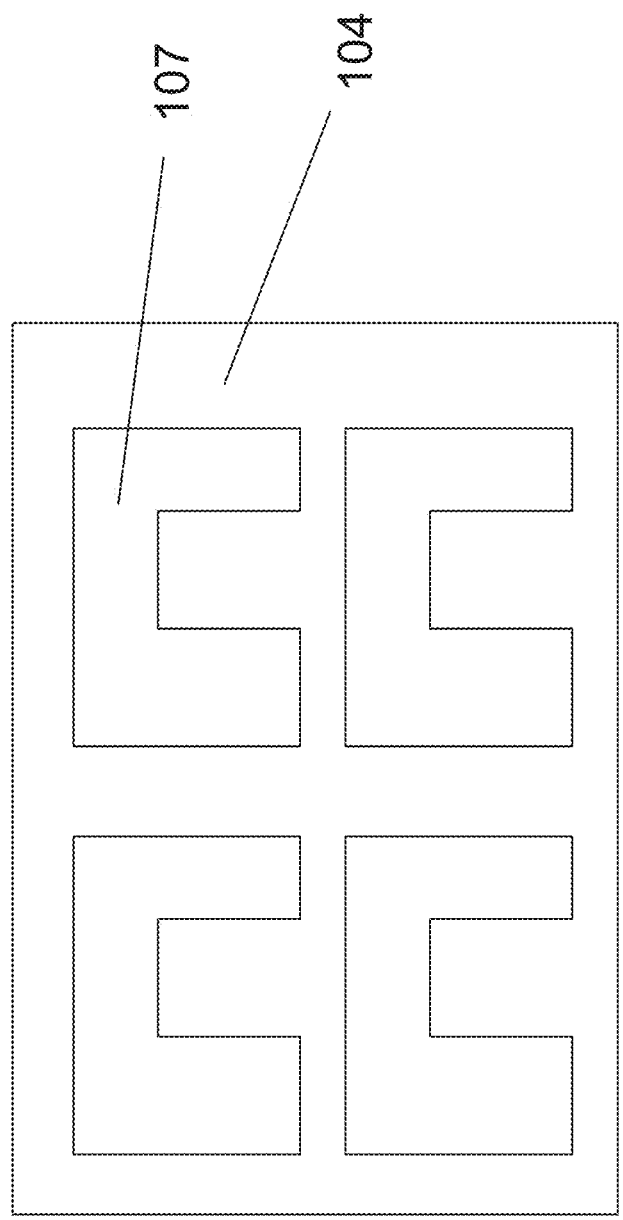
FIG. 8c shows a further alternative top view.

FIG. 8c shows a further alternative top view of an ISFET arrangement having an array of ISFETs. Only the passivation layer 104 and the recess 107 are shown. In this embodiment, the structure/shape of the recess 107 is different from that shown in FIG. 8b. It will be appreciated that the structure/shape of the recess 107 is not limited to a regular structure/shape such as a rectangular or circular structure/shape.

It will be noted that the first and second embodiments described above are directed to arrangements having the recess formed directly on the surface of the gate. It will be appreciated that alternatively the recess may be arranged such that it is not located directly on the surface of the gate. For example, the recess can be formed on the surface of IMD 112 so that IMD 112 and ILD 111 are between the recess and the gate. It may be also possible that the recess is formed such that the surface of the recess is located above inter metals 131, 131a, 132 and 132a but below top inter metals 133 and 133a. In such an arrangement, there may be a further inter metal above inter metals 131, 131a, 132 and 132a and below top inter metals 133 and 133a, and the recess is located above the further inter metal but below the top inter metals 133 and 133a.

It will be also noted that the foregoing description is generally directed to arrangements having a poly gate. It will be appreciated that the poly gate may comprise poly silicon or any other semiconductor materials.

It will be also noted that the first and second embodiments described above are directed to ISFET arrangements which are manufactured using a CMOS manufacturing process. It will be appreciated that the ISFET arrangements can also be manufactured using standard bipolar processing steps.

Although the invention has been described in terms of preferred embodiments as set forth above, it should be understood that these embodiments are illustrative only and that the claims are not limited to those embodiments. Those skilled in the art will be able to make modifications and alternatives in view of the disclosure which are contemplated as falling within the scope of the appended claims. Each feature disclosed or illustrated in the present specification may be incorporated in the invention, whether alone or in any appropriate combination with any other feature disclosed or illustrated herein.

The invention claimed is:

1. A CMOS or bipolar based Ion Sensitive Field Effect Transistor (ISFET) comprising:
   an ion sensitive recess for holding a liquid wherein the recess is formed at least partly on top of a gate of the transistor,
   a dielectric material over a semiconductor substrate comprising a drain and a source wherein the dielectric material is in contact with, or surrounds, the recess, and
   wherein the dielectric material further includes an inter-layer dielectric on top of the substrate, the inter-layer dielectric at least partially covering the gate.

2. An ISFET according to claim 1, wherein the recess is formed directly on top of the gate.

3. An ISFET according to claim 1, wherein at least one layer is formed between the recess and the gate, the at least one layer comprising a material comprising any of titanium nitride, silicon oxide nitride, silicon oxide or a metal.

4. An ISFET according to claim 1, wherein the gate comprises an insulator.

5. An ISFET according to claim 1, wherein the gate comprises an insulator and poly gate on top of the insulator.

6. An ISFET according to claim 1, wherein the recess comprises an ion sensitive membrane.

7. An ISFET according to claim 1, wherein the dielectric material further comprises at least one inter-metal dielectric on top of the inter-layer dielectric.

8. An ISFET according to claim 1, wherein the ISFET is a bipolar based ISFET.

9. An ISFET according to claim 6, wherein the ion sensitive membrane is deposited on at least a portion of the surface defining the recess on top of the gate.

10. An ISFET according to claim 7, further comprising inter metals formed within the at least one inter-metal dielectric, the inter metals being connected separately with the source and drain by contact plugs.

11. An ISFET according to claim 10, wherein the recess is formed on top of the inter-layer dielectric.

12. An ISFET according to claim 10, wherein the recess is formed on top of a first inter-metal dielectric.

13. An ISFET according to claim 10 further comprising a passivation layer formed on top of the at least one inter-metal layer, wherein the passivation layer is in contact with, or surrounds, the recess.

14. A method of manufacturing an Ion Sensitive Field Effect Transistor (ISFET) utilizing CMOS or bipolar processing steps, the method comprising forming an ion sensitive recess for holding a liquid at least partly on top of a gate of the transistor, wherein the recess is formed by patterning a dielectric material on top of the gate and etching the dielectric material, and wherein the gate has direct contact with the recess.

15. A method according to claim 14, wherein the recess is formed directly on top of the gate.

16. A method according to claim 14, wherein the gate comprises an insulator.

17. A method according to claim 14, wherein the gate comprises an insulator and a poly gate on top of the insulator.

18. A method according to claim 14, wherein the recess is formed utilizing CMOS or bipolar processing steps.

19. A method of manufacturing an Ion Sensitive Field Effect Transistor (ISFET) utilizing CMOS or bipolar processing steps, the method comprising forming an ion sensitive recess for holding a liquid at least partly on top of a gate of the transistor, wherein the transistor comprises a CMOS or bipolar device having inter-layer metals, a dielectric region having dielectric layers and a passivation layer over a semiconductor substrate of the device, and wherein the gate has direct contact with the recess.

20. A method according to claim 19, wherein the CMOS or bipolar device is formed by:
   providing the semiconductor substrate having a source and a drain;
   providing the gate on top of the substrate between the source and the drain;
   providing the dielectric region comprising an inter-layer dielectric over the substrate and inter-metal dielectrics on top of the inter-layer dielectric;
   providing the inter-layer metals in each inter-layer dielectric over the source and drain, the inter-layer metals being connected separately with the source and drain by contact plugs and being connected with one another by inter-layer vias; and
   providing the passivation layer over the inter-layer metals and the inter-metal dielectrics.

21. A method according to claim 19, wherein the recess is formed by patterning the dielectric region on top of the gate and etching the dielectric layers of the dielectric region.

22. A method according to claim 21, wherein etching the dielectric region on top of the gate comprises:
   etching a portion of the passivation layer over the gate;
   etching a portion of the inter-metal dielectrics over the gate; and
   etching a portion of the inter-layer dielectric on top of the gate.

23. A method according to claim 21, wherein etching the dielectric region on top of the gate comprises:
   etching a portion of the passivation layer over the gate; and
   etching a portion of the inter-metal dielectrics over the gate.

24. A method of manufacturing an Ion Sensitive Field Effect Transistor (ISFET) utilizing CMOS or bipolar processing steps, the method comprising:
   forming an ion sensitive recess for holding a liquid at least partly on top of a gate of the transistor; and
   depositing an ion sensitive membrane on at least a portion of the surface defining the recess on top of the gate;
   wherein the gate has direct contact with the recess.

25. An assembly comprising:
   a CMOS or bipolar based Ion Sensitive Field Effect Transistor (ISFET) comprising an ion sensitive recess for holding a liquid wherein the recess is formed at least partly on top of a gate of the transistor, and
   a circuit for reading out a signal from the ISFET,
   wherein the circuit and the ISFET are integrated within a same chip, and
   wherein the gate has direct contact with the recess.

* * * * *